(12) United States Patent
Kang et al.

(10) Patent No.: US 8,192,686 B2
(45) Date of Patent: *Jun. 5, 2012

(54) APPARATUS FOR AND METHOD OF MEASURING BIO-CHIPS USING UNIFORM TOTAL INTERNAL REFLECTION ILLUMINATION

(75) Inventors: Uk Kang, Gyeonggi-do (KR); Soo Jin Bae, Gyeonggi-do (KR); Geri V. Papayan, Saint Petersburg (RU)

(73) Assignee: Korea Electro Technology Research Institute, Gyeongsangnam (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/221,482

(22) Filed: Aug. 30, 2011

(65) Prior Publication Data

US 2011/0315894 A1    Dec. 29, 2011

Related U.S. Application Data

(63) Continuation of application No. 11/810,915, filed on Jun. 7, 2007, now Pat. No. 8,017,079.

(30) Foreign Application Priority Data

Oct. 24, 2006   (KR) .................. 10-2006-0103330

(51) Int. Cl.
    *G01N 21/00*   (2006.01)
(52) U.S. Cl. ................................... 422/82.05
(58) Field of Classification Search .......... 422/82.05
    See application file for complete search history.

(56) References Cited

U.S. PATENT DOCUMENTS

| | | | |
|---|---|---|---|
| 3,825,349 A | 7/1974 | Nomarski | |
| 4,679,900 A | 7/1987 | McKechnie et al. | |
| 5,249,077 A * | 9/1993 | Laronga et al. | 359/385 |
| 5,734,498 A | 3/1998 | Krasieva et al. | |
| 6,620,623 B1 * | 9/2003 | Yershov et al. | 436/172 |
| 6,956,648 B2 | 10/2005 | Loicht et al. | |
| 7,307,802 B2 | 12/2007 | Unger | |
| 7,576,911 B1 | 8/2009 | Larimer | |
| 8,017,079 B2 * | 9/2011 | Kang et al. | 422/82.05 |

FOREIGN PATENT DOCUMENTS

KR   10-2004-0081733   4/2006

OTHER PUBLICATIONS

Online Dictionary Definition of Diffusor. Dec. 13, 2011. 1 page.*
English machine translaion of KR 10-2004-0081733 dated Apr. 21, 2010.
Facsimile of After Final Amendment to Claims May 3, 2011, 4 pages.

* cited by examiner

*Primary Examiner* — Bobby Ramdhanie
(74) *Attorney, Agent, or Firm* — Frommer Lawrence & Haug LLP; Ronald R. Santucci

(57) ABSTRACT

Disclosed herein is an apparatus for and method of measuring bio-chips, which can implement an illumination method of a novel type that illuminates a bio sample (which may be also referred to as a "bio specimen") through a side face of a substrate using a diffusion plate to form an evanescent field by the illumination light over the entire surface of a substrate so as to uniformly secure brightness of the illuminated light over a wide area of a substrate, thereby more efficiently measuring fluorescence information of a bio-chip over a wide field of view.

11 Claims, 3 Drawing Sheets

APPARATUS FOR AND METHOD OF MEASURING BIO-CHIPS USING UNIFORM TOTAL INTERNAL REFLECTION ILLUMINATION

CROSS-REFERENCE TO RELATED APPLICATIONS

This application is a continuation of U.S. patent application Ser. No. 11/810,915 filed Jun. 7, 2007 entitled "Apparatus for and Method of Measuring Bio-Chips Using Uniform Total Internal Reflection Illumination" and issued as U.S. Pat. No. 8,017,079 on Sep. 13, 2011, which claims the benefit under 35 U.S.C. §119(a) of Korean Patent Application No. 10-2006-0103330, filed in the Korean Intellectual Property Office on Oct. 24, 2006, the entire disclosures of which are incorporated herein by reference.

BACKGROUND OF THE INVENTION

1. Field of the Invention

The present invention relates to an apparatus for and method of measuring bio-chips, and more particularly to an apparatus for and method of measuring bio-chips, which can implement an illumination method of a novel type that illuminates a bio sample (which may be also referred to as a "bio specimen") through a side face of a substrate using a diffusion plate so as to more efficiently measure fluorescence information of a bio-chip over a wide field of view.

2. Background of the Related Art

In general, a bio-chip refers to a chip including the arrangement of biological molecules such as DNA molecule, etc. The bio-chip is typically configured such that very small cells of a micro unit are plotted in the form of a matrix on a predetermined substrate.

A glass plate is generally used as the substrate and a substrate made of other material such as silicone may be used. A variety of DNA molecules are distributed on cells of an ultrafine size.

A bio-chip measurement apparatus is an instrument that is manufactured specially to measure fluorescence emitted from fine cells of a micro unit formed on the bio-chip and image the emitted fluorescence as an image. Such a bio-chip measurement apparatus enables acquisition of fluorescence observation image from micro cells and readout of information on the cells.

The bio-chip measurement apparatus can be classified into two types in terms of a measurement principle. One is a scanning-type measurement apparatus, and the other is such a measurement apparatus that observes an area of a to-be-measured object at a time such as a camera. In case of the former, information is sequentially read out from cells to cell.

In case of the latter, all the cells on the bio-chip covered by a field of view of a microscope are concurrently analyzed.

This type of bio-chip measurement apparatus is a merit that fluorescence information is obtained on a parallel basis from all the cells as to-be-measured objects, it is possible analyze data a relatively high speed as compared to the scanning type bio-chip measurement apparatus.

Moreover, since the latter type of bio-chip measurement apparatus generally has a relatively simple structure and is simple to operate as compared to the scanning-type bio-chip measurement apparatus, it is suitable for analysis of a large amount of data.

The latter type of bio-chip measurement apparatus adopting a total internal reflection illumination method is illustrated as its representative example in FIG. 1.

As shown in FIG. 1, a parallel-collimated excitation light emitted from a light source 10 is incident to a side face 13 of a substrate 12 on which bio samples 14 are placed. In this case, the bio-chip 11 is configured such that bio samples 14 are arranged on a thin transparent substrate 12 having a rectangular parallelepiped shape and a front face 15 on which bio samples 14 are arranged, a rear face 16 and a side face 13.

At this time, the excitation light emitted from the light source substrate is incident to the side face of the substrate at an incidence angle which can be defined through total internal reflection between the front face on which the bio samples are arranged and the rear face opposite to the front face. Meanwhile, fluorescence is observed from the bio samples by means of an evanescent field formed over the front face of the substrate on which the bio samples are arranged. The fluorescence observation image is observed and measured by a fluorescence detecting section 18, so that fluorescence information can be measured from the bio-chip.

However, such a conventional bio-chip measurement apparatus has a limitation in illumination to the bio sample when it is desired to measure fluorescence information of the bio-chip over a wide field of view.

If it is required that fluorescence information of the bio-chip should be measured over a wide field of view, a main factor that must be taken into consideration in the bio-chip measurement apparatus is uniformity of light with which to illuminate the bio samples to receive an identical signal from the same points positioned in various portions within a field of view for observation.

A main reason why brightness of light is ununiform is that flux of light illuminated is not even.

For example, as shown in FIG. 2, from the brightness distribution in a cross-section of a green laser beam excited and oscillated by a laser diode used in a bio-chip measurement apparatus using Cy3 as fluorescent dye, it can be seen that the brightness of the green laser beam is not uniform over the cross-section of the laser beam.

The brightness of the light is maximum at the central portion of the beam and is gradually decreased as it goes toward the peripheral portion of the beam.

In FIG. 2, the photo at the left side shows the brightness of a laser beam excited and oscillated by a laser diode and the graph at the right side shows brightness intensity of the laser beam.

Here, a white colored circle in the photo indicates a region where the brightness of the laser beam is as low as twice the maximum value.

In addition, in case where a laser beam is, at a predetermined inclination angle, incident to the front surface of the substrate on which samples of the bio-chip to be measured are placed in order to use the total internal reflection illumination method such as the above conventional bio-chip measurement apparatus, regions which are illuminated with the light are indicated with them divided into black-colored areas which progress at a certain incidence angle, which leads to a difficulty in illuminating the bio samples when it is desired to measure fluorescence information of the bio-chip over a wide field of view.

SUMMARY OF THE INVENTION

Accordingly, an aspect of exemplary embodiments of the present invention has been made to solve the aforementioned problems occurring in the prior art, and it is an object of the present invention to provide an apparatus for and method of measuring bio-chips, which can implement an illumination method of a novel type in which bio samples are illuminated with light emitted from a light source through a side face of a substrate using a diffusion plate so as to form an evanescent field over the entire surface of the substrate using an illumination light, thereby securing uniformity of brightness of the light to be irradiated to a wide area of the substrate and hence more efficiently measuring fluorescence information of a bio-chip over a wide field of view.

To accomplish the above object, according to one aspect of exemplary embodiments of the present invention, there is provided a bio-chip measurement apparatus for measuring fluorescence emitted from a bio-chip in which at least one or more bio samples are arranged on one surface of a thin rectangular parallelepiped-shaped substrate, the bio-chip measurement apparatus including: a bio-chip holder for supporting the bio-chip; an excitation light supply section for allowing an excitation light emitted therefrom to be incident to a side face of the substrate so as to be totally reflected inside the substrate to reach in the vicinity of the bio samples; a diffusion means disposed between the side face of the substrate and the excitation light supply section for inducing diffusion of the light to be incident to the substrate to allow the light totally reflected inside the substrate to form a uniform evanescent field over a wide range of area; a fluorescence detecting section disposed above the substrate for observing and detecting fluorescence emitted from the bio samples through the evanescent field formed by the light totally reflected inside the substrate.

Also, the bio-chip measurement apparatus may further include a iris diaphragm disposed at the upper and lower end portions of the side face of the substrate for interrupting a diffusion light having an incidence angle smaller than the critical angle of total internal reflection so as to prevent the diffusion light from entering the inside of the substrate.

Further, the bio-chip holder for supporting the bio-chip may be extended at a partial area thereof so as to serve to prevent a diffusion light having an incident angle smaller than the critical angle of total internal reflection from entering the inside of the substrate.

In addition, the excitation light supply section may include a first light source for allowing light emitted therefrom to be directly rectilinearly illuminated onto the side face of the substrate and a second light source for allowing light emitted therefrom to be illuminated onto a dichroic mirror and reflected by the surface of the dichroic mirror at a predetermined angle so as to be incident to the side face of the substrate.

Moreover, the excitation light supply section may include any one of a laser, an LED and a white light source as a light source.

Also, the diffusion means may include a diffuser having a volume or a diffusion film.

Further, the diffusion means may be positioned in the proximity of the side face of the substrate or directly may be positioned to abut against an interface of the side face of the substrate.

Also, the fluorescence detecting section may include objectives disposed symmetrically to each other with respect to an interference filter interposed between the objectives for removing a noise, and a fluorescence detector disposed in parallel with the objectives.

Further, the fluorescence detecting section may be disposed to confront the surface of the substrate on which the bio samples are arranged, or the surface opposite to the substrate surface on which the bio samples are arranged.

To accomplish the above object, according to another aspect of exemplary embodiments of the present invention, there is also provided a bio-chip measurement method for measuring fluorescence emitted from a bio-chip in which at least one or more bio samples are arranged on one surface of a thin rectangular parallelepiped-shaped substrate, the method including the steps of: (i) fixing the bio samples arranged on the substrate to a focal position and a field of view of objectives of a fluorescence detecting section; (ii) allowing an excitation light to be incident to a side face of the substrate so as to be totally reflected and advanced inside the substrate while being diffused and scattered through a diffusion plate disposed in front of the side face of the substrate; (iii) detecting fluorescence emitted from bio samples existing within an evanescent field 17 formed by the excitation light totally reflected inside the substrate; and (iv) analyzing an image formed by the detected fluorescence.

Also, the step (ii) further comprises a step of allowing a iris diaphragm means to interrupt a diffusion light having an incidence angle smaller than the critical angle of total internal reflection so as to prevent the diffusion light from entering the inside of the substrate 12.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

Reference will now be made in detail to a bio-chip measurement apparatus and method according to an embodiment of the present invention with reference to the attached drawings.

Figure 1:
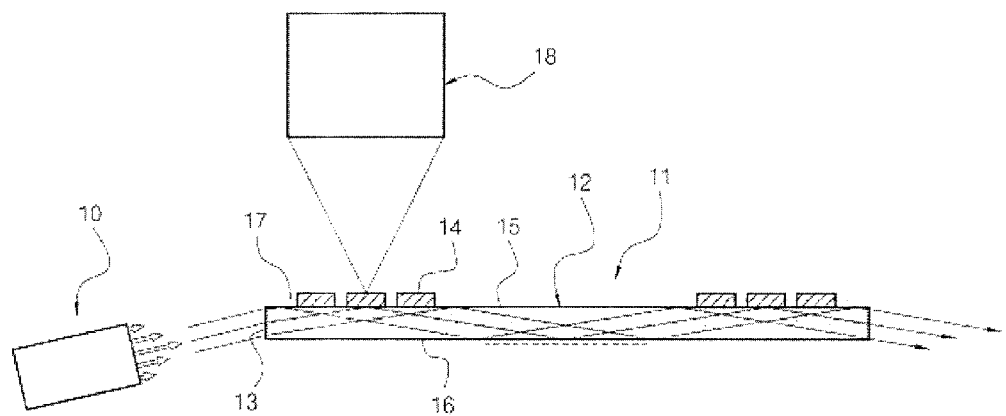
FIG. 1 is a schematic view illustrating a measurement principle of a conventional bio-chip measurement apparatus according to the prior art.
Figure 2:
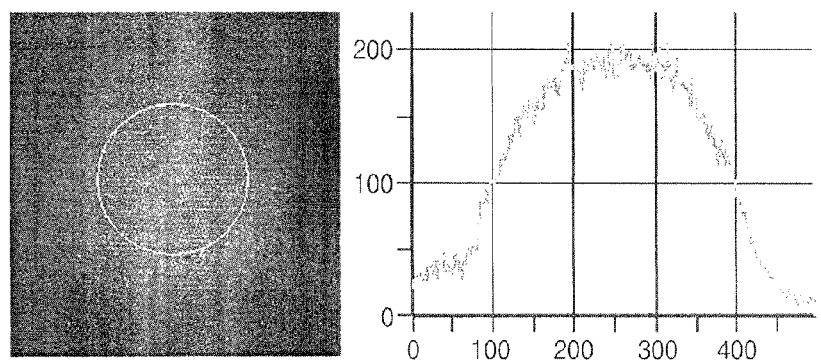
FIG. 2 is a photo and graph illustrating brightness intensity of a laser beam excited and oscillated by a laser diode.
Figure 3:
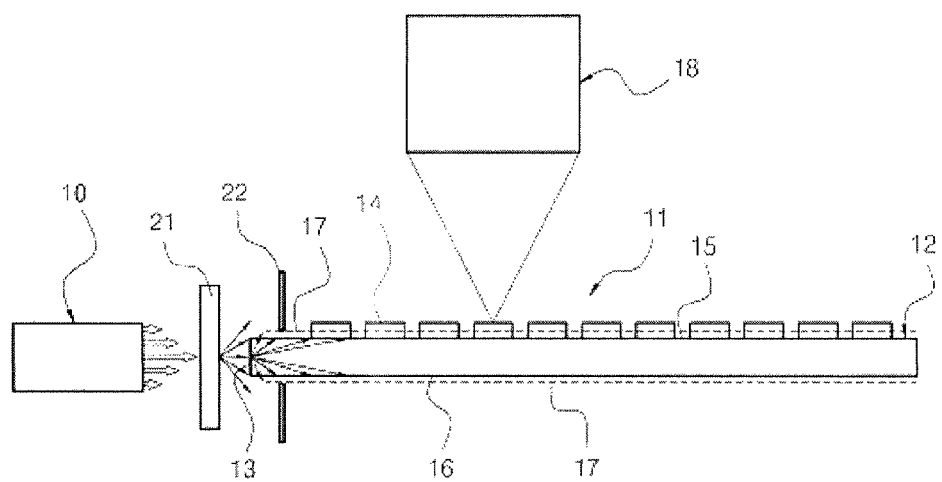
FIG. 3 is a schematic view illustrating a measurement principle of a bio-chip measurement apparatus according to the present invention.

FIG. 3 is a schematic view illustrating a measurement principle of a bio-chip measurement apparatus according to the present invention.

As shown in FIG. 3, the bio-chip measurement apparatus according to the present invention is configured so that when light is illuminated to a side face of a substrate to perform and is totally reflected inside a substrate, an area of the substrate to which the light is illuminated can be increased.

To this end, a parallel-collimated excitation light emitted from an excitation light supply section 10 is incident to a side face 13 of a substrate 12 of a bio-chip 11.

In this case, the bio-chip 11 includes a thin transparent rectangular parallelepiped-shaped substrate 12 having a front face 15, a rear face 16 and a side face 13, and bio specimens 14 arranged on the front face 15 of the substrate 12.

The light irradiated from the excitation light supply section 10 is incident to the side face 13 of the substrate 12 and then is advanced while being totally reflected inside the substrate 12 between a face on which the bio specimens 14 are arranged, i.e., the front face 15 and a face opposite to the front face, i.e., the rear face 16.

In more detail, in front of the side face 13 of the substrate 12 is disposed a diffusion plate 21 for diffusion and scattering of light to be incident to the substrate. At this time, diffusion action of the diffusion plate 21 enables the light incident to the substrate 12 to be totally reflected and advanced inside the substrate while forming an evanescent field 17 over the entire area of the substrate 12.

At this time, the diffusion plate can be supported by means of a known support structure using a bracket, etc.

A diffuser such as, for example, an opal glass or a diffusion film may used as the diffusion plate 21 having light transmission.

In this case, the diffusion plate must have high light transmission in order to reduce a loss of the illumination light, and a diffusion angel of the light must be wide in order to improve uniformity of illumination.

For example, a diffusion sheet used in a back light unit of a liquid crystal display (LCD) has such a property.

In addition, an iris diaphragm 22 is disposed at the upper and lower end of the side face 13 of the substrate 12 in such a fashion as to be vertically extended from the upper and lower end of the side face by a given area. In this case, the iris diaphragm 22 serves to interrupt some of light diffused by the diffusion plate 21 to prevent the interrupted light from entering the inside of the substrate 12 to thereby reduce a background noise.

As such, when the light incident to the side face of the substrate 12 is totally reflected and advanced inside the substrate 12, fluorescence is emitted from the front face 15 of the substrate 12 on which the bio specimens 14 are arranged by the evanescent field 17, and an image formed by the emitted fluorescence is detected through the fluorescence detecting section 18. That is, the fluorescence image is projected onto a detection surface of a high-sensitivity fluorescence detector 26 through the objectives mounted in the fluorescence detector 18.

At this time, in order to prevent the excitation light except for fluorescence from reaching the detection surface, an interference filter can be mounted at a proper position in the fluorescence detecting section 18.

Like this, in case where light is illuminated to the side face of the substrate to cause the illuminated light to undergo total internal reflection in the substrate, the bio-chip of a wide field of view can be illuminated by using diffusion and scattering action of the diffusion plate. Thus, it is possible to secure uniformity of brightness of the light illuminated to a wide area of the substrate.

Figure 4:
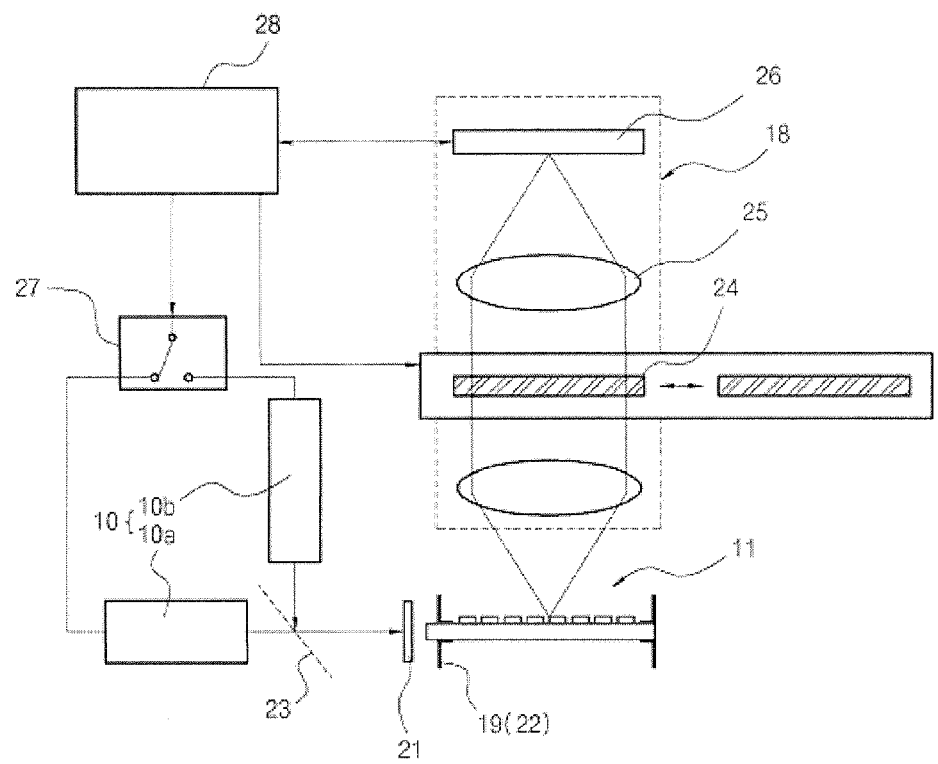
FIG. 4 is a schematic view illustrating a bio-chip measurement apparatus according to an embodiment of the present invention.

FIG. 4 is a schematic view illustrating a bio-chip measurement apparatus according to an embodiment of the present invention.

Referring to FIG. 4, in this embodiment, there is shown an illumination method in which light is illuminated to the side face of the substrate using the diffusion plate.

Bio specimens 14 prepared for fluorescence measurement are placed on one surface of a thin rectangular parallelepiped-shaped substrate 12, for example, the front face 15. At this time, the side face 13 of the substrate 12 is perpendicular to the front face.

The excitation light emitted from first and second light sources 10a and 10b of the excitation light supply section 10 passes through diffusion plate 21 before reaching the side face 13 of substrate 12 on which the bio specimens 14 are placed.

The light passing through the diffusion plate 21 is diffused and scattered, and then is incident to the side face 13 of the substrate 12. Thereafter, the light incident to the side face 13 passes through the inside of the substrate 12 and simultaneously causes the bio specimens 14 to emit fluorescence through the front face 15 or the rear face 16.

In this case, since the substrate 12 has a refractive index higher than the ambient medium (for example, glass refractive index is 1.5 and air refractive index is 1), it serves as a light guide plate for transferring light therethrough.

In addition, in case where the light incident to the side face 13 of the substrate 12 has an incidence angle larger than the critical angle of total internal reflection, it is again reflected by the front face 15 and the rear face 16 of the substrate 12 toward the inside of the substrate.

The bio specimens 14 emit fluorescence by the evanescent field 17 generated in the vicinity of the surfaces of the substrate 12, i.e., the front face 15 and the rear face 16, and the emitted fluorescence is detected by the fluorescence detecting section 18.

Meanwhile, since the light having an incidence angle smaller than the critical angle of total internal reflection is interrupted by the iris diaphragm 22 mounted at the upper and lower ends of the side face 13 of the substrate 12, it is prevented from entering the inside of the substrate 12 to thereby reduce the background noise.

The substrate 12 can employ a general microscope glass. The microscope glass preferably generates a small amount of its own intrinsic fluorescence in order to reduce the background noise generated from the microscope glass.

For example, the substrate 12 can adopt a microscope glass having a small amount of its own intrinsic fluorescence, which is manufactured by Corning Inc., in the US.

The bio specimens 14 may be placed on the front face 15 or the rear face 16 of the substrate 12.

In case where the bio specimens 14 are placed on the rear face 16 of the substrate 12, the fluorescence emitted from the bio specimens 14 pass through the substrate 12 and enters the fluorescence detecting section 18. Thus, in this case, the thickness of the substrate 12 must be taken into consideration upon the design of the optical system of the fluorescence detecting section 18.

In order to reduce a loss of the illumination light, the diffusion plate 21 is preferably disposed in the proximity of the side face 13 of the substrate 12. In a special case, a diffusion function element may be directly mounted at the interface of the side face 13 of the substrate 12.

The iris diaphragm 13 may be replaced with the structure employing the bio-chip holder 19 for supporting the bio specimen 14.

That is, the bio-chip holder 19 constructed to support both ends of the bio-chip can act as an iris diaphragm through a structure in which a portion adjacent to the side face of the substrate is partially extended vertically.

In order to measure fluorescence produced from the bio-chip 11 including a plurality of dyes, it is required to mount a plurality of laser light sources corresponding to a light absorption wavelength of a plurality of dyes.

In FIG. 4, there is shown one example for measurement of the fluorescence of the bio-chip including two dyes.

Here, the bio-chip 11 includes two fluorescence dyes such as for example Cy3 and Cy5.

Two different laser light sources 10a and 10b are needed to excite two fluorescence dyes.

In an embodiment of the present invention, two laser light sources were used which have a light absorption wavelength of 530 nm and 660 nm.

The light emitted from the laser light sources 10a and 10b converges in one direction through the dichroic mirror 23 and then is perpendicularly incident to the side face 13 of the substrate 12 on which the bio specimens 14 are arranged.

The diffusion plate 21 is disposed in an optical path of the side face of substrate 12 to which the laser beam is incident so that the laser beam incident to the side face 13 of the substrate 12 is uniformly diffused and scattered through diffusion plate 21.

This diffusing and scattering function of the diffusion plate can be implemented by two diffusion films (DFA) manufactured by 3M Company.

For example, one of these films is directly installed at the side face of the substrate and the other is installed at a distance 8 mm away from the side face of the substrate.

In addition, the bio-chip holder 19 supporting the bio-chip can adopt a known structure which supports both ends of the substrate 12 and allows the bio specimens 14 to be covered by a field of view of the objective 25 of the fluorescence detecting section 18.

In order to rapidly measure a large amount of bio samples, the bio-chip holder 19 preferably has a structure in which the substrate including bio samples is accurately fixed to a predetermined position even without performing a burdensome work of changing the position of the bio-chip so as to focus-match with an existing microscope.

The light incident to the inside of the substrate 12 from the side face of the substrate 12 supported by the bio-chip holder 19 enables a uniform evanescent field 17 to be formed over a wide range, i.e., a nearly overall surface of the substrate.

The excitation of the fluorescent dyes caused by the evanescent field 17 occurs uniformly irrespective of the position of the bio specimens placed on the substrate within a field of view of, for example, 6.4×4.8 mm.

The optical system of the fluorescence detecting section 18 for measuring fluorescence produced from the bio specimens converges a fluorescence signal and transmits the converged fluorescence signal to the fluorescence detector 26, i.e., a television camera enabling the detection of fluorescence.

Here, the fluorescence detector 26 may employ a CCD camera, a CMOS image sensor or the like, and may be configured to enable the position control or fixation with the objective using a spiral groove, etc.

At this time, the optical system has a symmetrical structure in which two opposed optical modules i.e., two objectives 25 are vertically disposed symmetrically with each other.

Further, an interference filter module, i.e., an interference filter 24 is installed at a parallel light path between the two objectives 25, and two interference filters 24 can be exchanged with each other depending on a measurement condition.

In addition, the wavelengths of two light sources 10a and 10b mounted in the excitation light supply section 10 is selected to correspond to the light absorption wavelength of the dyes. Each of the two light sources 10a and 10b is operated sequentially by a switch 27 under the control of a microcomputer, i.e., a controller 28.

In this case, a light source such as a semiconductor laser, etc., may be used in the excitation light supply section. Such a light source may include a laser as well as a white light source such as a lamp, etc., or an LED, etc.

Moreover, the interference filters can be exchanged in cooperation with the switch 27 for operation of the two light sources 10a and 10b.

These interference filters serves to separate fluorescence corresponding to dyes, and digital images of the fluorescence obtained through the optical system are sequentially applied to the controller 28 which in turn calculates fluorescence intensity within a bio-chip dot matrix and images its result as an image.

Here, the control of the light source by the controller, the exchange of the interference filters associated with the operation of the switch, calculation and imaging of fluorescence intensity by the controller can be adopted without a special limitation as far as being typically known in the prior art.

Therefore, the excitation light supply section, the fluorescence detecting section and the bio-chip holder including the bio-chip of the inventive bio-chip measurement apparatus can be fixed to a common support or case, and can include a specimen entrance mounted with a lid for allowing a bio-chip to be drawn in therethrough from a side portion of the apparatus. In this case, the specimen entrance may be configured to be closed by a locking device so as to block light from the outside from entering the apparatus.

In this state, the excitation light emitted from the laser light source passes through the diffusion plate and is incident to the side face of the substrate. This incident light is totally reflected and advanced inside the substrate.

Subsequently, the evanescent field enables fluorescence to be produced uniformly over a wide area of the substrate front face on which the bio specimens are arranged.

At this time, since the light emitted from the laser light source is incident to the side face of the substrate in the form of light diffused and scattered by the diffusion plate, a uniform evanescent field is formed over a wide area inside the substrate, which enables fluorescence information of the bio-chip to be effectively measured over a wide field of view.

The fluorescence emitted from the bio specimens existing within the evanescent field is emitted through the front face of the substrate. This fluorescence emitted through the front face is observed by the fluorescence detecting section.

That is, the evanescent field allows fluorescence to be produced from the substrate front face on which the bio specimens are arranged, and an image formed by the produced fluorescence is observed by the fluorescence detecting section. At this time, the fluorescence observation image is projected to a detection surface of the high-sensitivity fluorescence detector through the objectives mounted in the fluorescence detecting section.

Resultantly, digital images of the obtained fluorescence are sequentially applied to the controller which in turn calculates fluorescence intensity within a bio-chip dot matrix and images its result as an image, thereby completing the measurement of the bio-chip.

As described above, according to the present invention, it is possible to implement an illumination method of a novel type that illuminates a bio sample through a side face of a substrate using a diffusion plate so as to uniformly secure brightness of light over a wide area of a substrate, thereby more efficiently measuring fluorescence information of a bio-chip over a wide field of view.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A bio-chip measurement apparatus for measuring fluorescence emitted from a bio-chip 11 in which at least one or more bio samples 14 are arranged on one surface of a thin rectangular parallelepiped-shaped substrate 12, comprising:
    a bio-chip 11;
    a bio-chip holder 19 for supporting the bio-chip 11;
    an excitation light supply section 10 for allowing an excitation light emitted therefrom to be incident to a side face 13 of the substrate 12 so as to be totally reflected inside the substrate 12 to reach in the vicinity of the bio samples 14;

a diffusion plate 21 disposed between the side face 13 of the substrate 12 and the excitation light supply section 10 for inducing diffusion of the light to be incident to the substrate 12 to allow the light totally reflected inside the substrate 12 to form a uniform evanescent field 17 over a wide range of area;

a fluorescence detecting section 18 disposed above the substrate 12 for observing and detecting fluorescence emitted from the bio samples 14 through the evanescent field 17 formed by the light totally reflected inside the substrate 12; and an iris diaphragm 22 mounted at the upper and lower end portions of the side face 13 of the substrate 12 for preventing a diffusion light having an incidence angle smaller than the critical angle of total internal reflection from entering the inside of the substrate 12.

2. The bio-chip measurement apparatus according to claim 1, wherein the bio-chip holder 19 for supporting the bio-chip 11 is extended at a partial area thereof so as to serve to prevent a diffusion light having a critical angle smaller than the critical angle of total internal reflection from entering the inside of the substrate 12.

3. The bio-chip measurement apparatus according to claim 1, wherein the excitation light supply section 10 comprises a first light source 10a for allowing light emitted therefrom to be directly rectilinearly illuminated onto the side face 13 of the substrate 12 and a second light source 10b for allowing light emitted therefrom to be illuminated onto a dichroic mirror 23 and reflected by the surface of the dichroic mirror 23 at a predetermined angle so as to be incident to the side face 13 of the substrate 12.

4. The bio-chip measurement apparatus according to claim 1, wherein the excitation light supply section 10 comprises any one of a laser, an LED and a white light source as a light source.

5. The bio-chip measurement apparatus according to claim 1, wherein the diffusion plate 21 comprises either a diffuser having a volume or a diffusion film.

6. The bio-chip measurement apparatus according to claim 1, wherein the diffusion plate 21 is positioned in the proximity of the side face 13 of the substrate 12 or is positioned to directly abut against an interface of the side face of the substrate 12.

7. The bio-chip measurement apparatus according to claim 1, wherein the fluorescence detecting section 18 comprises objectives 25 disposed symmetrically to each other with respect to an interference filter 24 interposed between the objectives 25 for removing a noise and a fluorescence detector 26 disposed in parallel with the objectives 25.

8. The bio-chip measurement apparatus according to claim 1, wherein the fluorescence detecting section 18 is disposed to confront the surface of the substrate 12 on which the bio samples 14 are arranged, or the surface opposite to the substrate surface on which the bio samples 14 are arranged.

9. The bio-chip measurement apparatus according to claim 3 wherein the excitation light supply section 10 comprises any one of a laser, an LED and a white light source as a light source.

10. The bio-chip measurement apparatus according to claim 6, wherein the diffusion plate 21 is positioned in the proximity of the side face 13 of the substrate 12 or is positioned to directly abut against an interface of the side face of the substrate 12.

11. The bio-chip measurement apparatus according to claim 8, wherein the fluorescence detecting section 18 is disposed to confront the surface of the substrate 12 on which the bio samples 14 are arranged, or the surface opposite to the substrate surface on which the bio samples 14 are arranged.

* * * * *